United States Patent
Ura et al.

(10) Patent No.: US 7,196,207 B2
(45) Date of Patent: Mar. 27, 2007

(54) METHOD FOR PRODUCING 2-ALKYL-3-AMINOTHIOPHENE DERIVATIVE

(75) Inventors: Daisuke Ura, Omuta (JP); Hiroyuki Katsuta, Mobara (JP); Toshio Kitashima, Omuta (JP); Kenichi Sato, Omuta (JP)

(73) Assignee: Mitsui Chemicals, Inc., Tokyo (JP)

( * ) Notice: Subject to any disclaimer, the term of this patent is extended or adjusted under 35 U.S.C. 154(b) by 247 days.

(21) Appl. No.: 10/517,494

(22) PCT Filed: Jul. 22, 2003

(86) PCT No.: PCT/JP03/09249
§ 371 (c)(1),
(2), (4) Date: Dec. 10, 2004

(87) PCT Pub. No.: WO2004/009581
PCT Pub. Date: Jan. 29, 2004

(65) Prior Publication Data
US 2005/0176971 A1    Aug. 11, 2005

(30) Foreign Application Priority Data
Jul. 24, 2002   (JP) .............................. 2002-215281

(51) Int. Cl.
*C07D 333/36*   (2006.01)
(52) U.S. Cl. ...................................... 549/69
(58) Field of Classification Search ................... 549/69
See application file for complete search history.

(56) References Cited

U.S. PATENT DOCUMENTS

| | | | | | |
|---|---|---|---|---|---|
| 5,698,581 | A | * | 12/1997 | Kleemann et al. | 514/447 |
| 5,747,518 | A | * | 5/1998 | Yoshikawa et al. | 514/403 |
| 6,143,777 | A | * | 11/2000 | Jonas et al. | 514/447 |
| 6,331,639 | B2 | * | 12/2001 | Katsuta et al. | 549/69 |
| 6,790,866 | B2 | * | 9/2004 | Ohuchida et al. | 514/604 |
| 6,835,745 | B2 | * | 12/2004 | Coghlan et al. | 514/448 |

FOREIGN PATENT DOCUMENTS

| | | |
|---|---|---|
| EP | 1036793 A2 | 9/2000 |
| JP | 6-65107 A | 3/1994 |
| JP | 8-134009 A | 5/1996 |
| JP | 2002-53575 A | 2/2002 |
| WO | 94/07850 A1 | 4/1994 |

* cited by examiner

*Primary Examiner*—Deborah C. Lambkin
(74) *Attorney, Agent, or Firm*—Buchanan, Ingersoll & Rooney, PC

(57) ABSTRACT

A method for reducing a sulfur-containing compound by hydrogenation using a noble metal catalyst which method is exemplified by an industrial method for producing a 2-alkyl-3-aminothiophene derivative with high economical efficiency by hydrogenating a 2-alkenyl-3-aminothiophene derivative using the noble metal catalyst. 2-Alkyl-3-aminothiophene derivatives are useful compounds in the fields of medicine and agriculture, and in particular, useful in bactericides for agriculture or gardening, or intermediates of the bactericides. The hydrogenation reaction temperature is controlled at 150° C. to 300° C. and the method allows the used noble metal catalyst to be recovered and reused.

24 Claims, No Drawings

METHOD FOR PRODUCING 2-ALKYL-3-AMINOTHIOPHENE DERIVATIVE

TECHNICAL FIELD

The present invention relates to a method for reducing a sulfur-containing compound by hydrogenation using a noble metal catalyst. The present invention also relates to a method for producing a 2-alkyl-3-aminothiophene derivative, which is useful in bactericides for agriculture or gardening, or an intermediate of the bactericides.

BACKGROUND ART

According to Japanese Examined Patent Application Publication No. 8-32702, sulfur, and in particular, a thiophene, generally inactivates all hydrogenation catalysts to a significant degree.

In particular, according to a paper written by Mozingo [Journal of the American Chemical Society (J. Am. Chem. Soc.) Vol. 67, p. 2092 (1945)], a thiophene can be converted to a thiolane with a yield of 70%. However, this reaction requires 200% of a palladium catalyst to be added to the substrate. The use of this method on an industrial scale is economically disadvantageous.

Furthermore, it is known that a thiophene itself becomes a catalyst poison in catalytic hydrogenation of the thiophene ["Shokubai Kagaku Gairon" (Outline of Catalytic Chemistry) written by Tadao Shiba and two others, New edition, p. 121, 1956].

For the above reasons, in the reduction of a thiophene derivative by hydrogenation, a reaction example using a catalyst, which is a noble metal such as palladium without further treatment or a palladium catalyst carried on a support such as activated carbon, has rarely been described.

Japanese Unexamined Patent Application Publication No. 2000-327678 discloses the hydrogenation of a 2-alkenyl-3-aminothiophene derivative using a 5%-palladium carbon. The 2-alkenyl-3-aminothiophene derivative is represented by general formula (1):

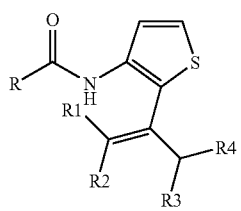

(1)

(wherein R represents a hydrogen atom, a substituted or unsubstituted alkyl group, a substituted or unsubstituted alkoxy group, a substituted or unsubstituted aromatic hydrocarbon ring, a substituted or unsubstituted nonaromatic hydrocarbon ring, a substituted or unsubstituted aromatic heterocycle, or a substituted or unsubstituted nonaromatic heterocycle; R1, R2, R3, and R4 independently represent a hydrogen atom, or a linear or branched alkyl group of 1 to 12 carbon atoms; and R1 and R2, R3 and R4, R1 and R3, R1 and R4, R2 and R3, or R2 and R4 may be bonded together to form a cycloalkyl group). In the above hydrogenation, the content of the catalyst relative to the compound is about 10%. The recovery and the reuse of the catalyst are not described in the document. However, such a reaction, wherein no less than 10% of the catalyst is used in every reaction, cannot be performed economically on an industrial scale.

DISCLOSURE OF INVENTION

It is an object of the present invention to provide an economically advantageous method for producing a sulfur-containing compound such as a 2-alkyl-3-aminothiophene derivative, which is useful in bactericides for agriculture or gardening, or an intermediate of the bactericides on an industrial scale. In the present invention, a noble metal catalyst is used to reduce a sulfur-containing compound such as a 2-alkenyl-3-thiophene derivative by hydrogenation; furthermore, the used noble metal catalyst is recovered and then reused.

In order to solve the above problems, as a result of intensive study, the present inventors have found the following facts and accomplished the present invention: It is fundamentally difficult to reduce thiophene derivatives by hydrogenation. Contrary to expectations, the reaction carried out at a relatively high reaction temperature prevents the inactivation of the used noble metal catalyst. As a result, the used noble metal catalyst can be recovered and reused.

In the present invention, a sulfur-containing compound is subjected to catalytic hydrogenation using a noble metal catalyst, and the used noble metal catalyst is then recovered. The recovered catalyst can be reused for the same reaction. The present invention includes the following two items: A sulfur-containing compound is subjected to catalytic hydrogenation using a noble metal catalyst, and the noble metal catalyst is then recovered for reuse in the same hydrogenation. In addition, when a sulfur-containing compound is subjected to catalytic hydrogenation using a noble metal catalyst, the noble metal catalyst recovered from the above catalytic hydrogenation can be used as a part or all of the noble metal catalyst in a future reaction.

The present invention includes the following Items:

[1] A method for reducing a sulfur-containing compound by hydrogenation, the method including the steps of hydrogenating the sulfur-containing compound using a noble metal catalyst at a reaction temperature of 150° C. to 300° C., recovering the used noble metal catalyst, and reusing the noble metal catalyst.

[2] The method for producing a 2-alkyl-3-aminothiophene derivative according to Item [1], wherein the noble metal catalyst is composed of palladium.

[3] The method for producing a 2-alkyl-3-aminothiophene derivative according to Item [1], wherein an alcohol of 1 to 8 carbon atoms is used as a reaction solvent in the step of hydrogenating the sulfur-containing compound.

[4] The method according to any one of Items [1] to [3], wherein the sulfur-containing compound is a thiophene compound.

[5] The method according to Item [4], wherein the thiophene compound is a thiophene amide.

[6] The method according to claim 5, wherein the thiophene amide is represented by general formula (1):

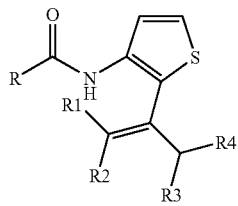

(wherein R represents a hydrogen atom, a substituted or unsubstituted alkyl group, a substituted or unsubstituted alkoxy group, a substituted or unsubstituted aromatic hydrocarbon ring, a substituted or unsubstituted nonaromatic hydrocarbon ring, a substituted or unsubstituted aromatic heterocycle, or a substituted or unsubstituted nonaromatic heterocycle; R1, R2, R3, and R4 independently represent a hydrogen atom, or a linear or branched alkyl group of 1 to 12 carbon atoms; and R1 and R2, R3 and R4, R1 and R3, R1 and R4, R2 and R3, or R2 and R4 may be bonded together to form a cycloalkyl group), and an alkenyl group of the compound represented by general formula (1) is reduced by hydrogenation to produce a 2-alkyl-3-aminothiophene derivative represented by general formula (2):

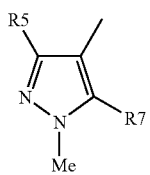

(wherein R, R1, R2, R3, and R4 are as defined above).

[7] The method according to Item [6], wherein R in the compounds represented by general formula (1) and general formula (2) is a hydrogen atom, a substituted or unsubstituted alkyl group, a substituted or unsubstituted alkoxy group, or a substituted or unsubstituted phenyl group.

[8] The method according to Item [6], wherein R in the compounds represented by general formula (1) and general formula (2) is a group represented by general formulae (A1) to (A12):

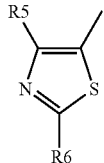

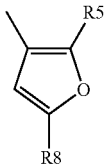

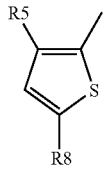

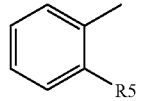

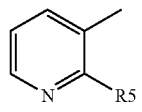

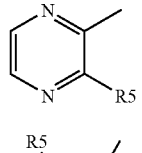

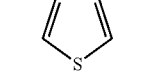

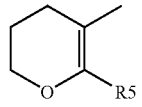

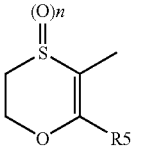

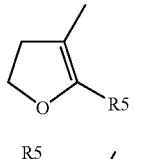

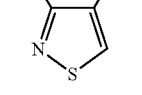

(wherein R5 represents a trifluoromethyl group, a difluoromethyl group, a methyl group, an ethyl group, a hydrogen atom, or a halogen atom; R6 represents a hydrogen atom, a methyl group, a trifluoromethyl group, a halogen atom, a methoxy group, or an amino group; R7 represents a hydrogen atom, a halogen atom, a methyl group, or a methoxy group; R8 represents a hydrogen atom, a methyl group, an ethyl group, or a halogen atom; and n represents an integer of 0 to 2; however, in general formulae (A9), (A10), and (A11), R5 does not represent a halogen atom).

[9] The method according to Item [8], wherein R in the compounds represented by general formula (1) and general formula (2) is represented by general formula (A1) in which R5 is a trifluoromethyl group and R7 is a hydrogen atom.

[10] The method according to Item [6], wherein each of R1, R2, and R3 in the compound represented by general formula (2) is a hydrogen atom and R4 in the compound represented by general formula (2) is an isopropyl group.

BEST MODE FOR CARRYING OUT THE INVENTION

The present invention will now be described in detail.

In the present invention, a sulfur-containing compound represents a substance having both a sulfur atom and an alkenyl chain in the molecule, and examples of the sulfur-containing compound according to the present invention include a thiophene compound. In the present invention, the thiophene compound represents a substance having both a thiophene ring and an alkenyl chain in the molecule, preferably, a compound having a carbon double bond conjugated with the thiophene ring, the double bond portion being reduced by hydrogenation. Examples of the thiophene compound include a thiophene amide. In the present invention, the thiophene amide represents a compound produced by a condensation reaction of a 2-alkenyl-3-aminothiophene and a carboxylic acid compound. Typical examples of the thiophene amide include a compound represented by general formula (1).

In the present invention, R in general formulae (1) and (2) may be a hydrogen atom. In the substituted or unsubstituted alkyl group represented by R, examples of the alkyl group include methyl, ethyl, propyl, isopropyl, butyl, isobutyl, sec-butyl, tert-butyl, hexyl, decyl, methoxymethyl, ethoxymethyl, and phenylmethyl groups.

In the substituted or unsubstituted alkoxy group represented by R, examples of the alkoxy group include methoxy, ethoxy, propoxy, isopropoxy, cyclopropoxy, butoxy, isobutoxy, sec-butoxy, tert-butoxy, cyclohexyloxy, hexyloxy, and benzyloxy groups.

Examples of the substituted or unsubstituted aromatic hydrocarbon ring represented by R include phenyl and substituted phenyl groups. Examples of the substituent of the substituted phenyl group include alkyl groups such as methyl, ethyl, propyl, and isopropyl groups; alkoxy groups such as methoxy, ethoxy, propoxy, and isopropoxy groups; halogen atoms such as chlorine, bromine, fluorine, and iodine atoms; a nitro group; a cyano group; and an amino group.

In the substituted or unsubstituted nonaromatic hydrocarbon ring represented by R, examples of the nonaromatic hydrocarbon ring include cyclopropyl, cyclopentyl, cyclohexyl, and cyclohexenyl groups. Examples of the substituent of the substituted nonaromatic hydrocarbon ring include the same substituents as those of the above substituted phenyl group.

Examples of the substituted or unsubstituted aromatic heterocycle represented by R include pyrazolyl, thiazolyl, isothiazolyl, furyl, thienyl, pyridyl, pyrazinyl, oxazolyl, pyrrolyl, substituted pyrazolyl, substituted thiazolyl, substituted isothiazolyl, substituted furyl, substituted thienyl, substituted pyridyl, substituted pyrazinyl, substituted oxazolyl, and substituted pyrrolyl groups. Examples of the substituent of the substituted pyrazolyl, substituted thiazolyl, substituted isothiazolyl, substituted furyl, substituted thienyl, substituted pyridyl, substituted pyrazinyl, substituted oxazolyl, and substituted pyrrolyl groups include alkyl groups such as methyl, ethyl, propyl, and isopropyl groups; haloalkyl groups such as trifluoromethyl and difluoromethyl groups; halogen atoms such as fluorine, chlorine, bromine, and iodine atoms; an amino group; and a cyano group.

Examples of the substituted or unsubstituted nonaromatic heterocycle represented by R include dihydropyranyl, dihydrofuryl, tetrahydrofuryl, 2,3-dihydro-1,4-oxathiin-5-yl, substituted dihydropyranyl, substituted dihydrofuryl, substituted tetrahydrofuryl, and substituted 2,3-dihydro-1,4-oxathiin-5-yl groups. Examples of the substituent of the substituted dihydropyranyl, substituted dihydrofuryl, substituted tetrahydrofuryl, and substituted 2,3-dihydro-1,4-oxathiin-5-yl groups include alkyl groups such as methyl, ethyl, propyl, and isopropyl groups; haloalkyl groups such as trifluoromethyl and difluoromethyl groups; halogen atoms such as fluorine, chlorine, and iodine atoms; an amino group; and a cyano group.

When R is represented by general formula (A1), the general formula (A1) represents a 4-pyrazolyl group in which R5 at the third position represents a trifluoromethyl group, a difluoromethyl group, a methyl group, an ethyl group, or a halogen atom; R7 at the fifth position represents a hydrogen atom, a halogen atom, a methyl group, or a methoxy group; and the first position is replaced with a methyl group. Examples of such a 4-pyrazolyl group include a 1,3-dimethyl-4-pyrazolyl group, 5-chloro-1,3-dimethyl-4-pyrazolyl group, 5-chloro-1-methyl-3-trifluoromethyl-4-pyrazolyl group, 1-methyl-3-trifluoromethyl-4-pyrazolyl group, 1-methyl-3-difluoromethyl-4-pyrazolyl group, 1-methyl-3-ethyl-4-pyrazolyl group, 1-methyl-3-chloro-4-pyrazolyl group, and 1-methyl-3-trifluoromethyl-5-methoxy-4-pyrazolyl group.

When R is represented by general formula (A2), the general formula (A2) represents a 5-thiazolyl group in which R5 at the fourth position represents a trifluoromethyl group, a difluoromethyl group, a methyl group,. an ethyl group, or a halogen atom; and R6 at the second position represents a hydrogen atom, a methyl group, a trifluoromethyl group, a halogen atom, a methoxy group, or an amino group. Examples of such a 5-thiazolyl group include a 2-methyl-4-trifluoromethyl-5-thiazolyl group, 2-methyl-4-difluoromethyl-5-thiazolyl group, 4-trifluoromethyl-5-thiazolyl group, 2,4-dimethyl-5-thiazolyl group, 2-methyl-4-ethyl-5-thiazolyl group, 2-amino-4-methyl-5-thiazolyl group, 2-methoxy-4-methyl-5-thiazolyl group, and 2-chloro-4-methyl-5-thiazolyl group.

When R is represented by general formula (A3), the general formula (A3) represents a 3-furyl group in which R5 at the second position represents a trifluoromethyl group, a difluoromethyl group, a methyl group, an ethyl group, or a halogen atom; and R8 at the fifth position represents a hydrogen atom, a methyl group, an ethyl group, or a halogen atom. Examples of such a 3-furyl group include a 2-methyl-3-furyl group, 2,5-dimethyl-3-furyl group, 2-chloro-3-furyl group, and 2-trifluoromethyl-3-furyl group.

When R is represented by general formula (A4), the general formula (A4) represents a 2-thienyl group in which R5 at the third position represents a trifluoromethyl group, a difluoromethyl group, a methyl group, an ethyl group, or a halogen atom; and R8 at the fifth position represents a hydrogen atom, a methyl group, or a halogen atom. Examples of such a 2-thienyl group include a 3-methyl-2-thienyl group, 3,5-dimethyl-2-thienyl group, 3-chloro-2-thienyl group, and 3-iodo-2-thienyl group.

When R is represented by general formula (A5), the general formula (A5) represents a phenyl group in which R5 at the second position represents a trifluoromethyl group, a difluoromethyl group, a methyl group, an ethyl group, or a halogen atom. Examples of such a phenyl group include a 2-trifluoromethylphenyl group, 2-difluoromethylphenyl group, 2-methylphenyl group, 2-ethylphenyl group, 2-fluorophenyl group, 2-chlorophenyl group, 2-bromophenyl group, and 2-iodophenyl group.

When R is represented by general formula (A6), the general formula (A6) represents a 3-pyridyl group in which R5 at the second position represents a trifluoromethyl group, a difluoromethyl group, a methyl group, an ethyl group, or a halogen atom. Examples of such a 3-pyridyl group include a 2-trifluoromethyl-3-pyridyl group, 2-difluoromethyl-3-pyridyl group, 2-methyl-3-pyridyl group, 2-ethyl-3-pyridyl group, 2-fluoro-3-pyridyl group, 2-chloro-3-pyridyl group, 2-bromo-3-pyridyl group, and 2-iodo-3-pyridyl group.

When R is represented by general formula (A7), examples of the functional group represented by general formula (A7) includes a 2-chloro-3-pyrazinyl group. When R is represented by general formula (A8), the general formula (A8) represents a 4-thienyl group in which R5 at the third position represents a trifluoromethyl group, a difluoromethyl group, a methyl group, an ethyl group, or a halogen atom. Examples of such a 4-thieny group include a 3-trifluoromethyl-4-thienyl group, 3-difluoromethyl-4-thienyl group, 3-methyl-4-thienyl group, 3-ethyl-4-thieny group, 3-fluoro-4-thieny group, 3-chloro-4-thieny group, 3-bromo-4-thieny group, and 3-iodo-4-thieny group.

When R is represented by general formula (A9), the general formula (A9) represents a 3,4-dihydro-2H-pyran-5-yl group in which R5 at the sixth position represents a trifluoromethyl group, a difluoromethyl group, a methyl group, or an ethyl group. Examples of such a 3,4-dihydro-2H-pyran-5-yl group include a 6-trifluoromethyl-3,4-dihydro-2H-pyran-5-yl group, 6-difluoromethyl-3,4-dihydro-2H-pyran-5-yl group, 6-methyl-3,4-dihydro-2H-pyran-5-yl group, and 2-ethyl-3,4-dihydro-2H-pyran-5-yl group.

When R is represented by general formula (A10), the general formula (A10) represents a 2,3-dihydro-1,4-oxathiin-5-yl group, a 2,3-dihydro-1,4-oxathiin-4-oxido-5-yl group, or a 2,3-dihydro-1,4-oxathiin-4,4-dioxido-5-yl group in which R5 at the sixth position represents a trifluoromethyl group, a difluoromethyl group, a methyl group, or an ethyl group. Examples of such a functional group include a 6-methyl-2,3-dihydro-1,4-oxathiin-5-yl group, 6-methyl-2,3-dihydro-1,4-oxathiin-4-oxido-5-yl group, and 6-methyl-2,3-dihydro-1,4-oxathiin-4,4-dioxido-5-yl group.

When R is represented by general formula (A11), the general formula (A11) represents a 2,3-dihydro-4-furyl group in which R5 at the fifth position represents a trifluoromethyl group, a difluoromethyl group, a methyl group, or an ethyl group. Examples of such a 2,3-dihydro-4-furyl group include a 5-trifluoromethyl-2,3-dihydro-4-furyl group, 5-difluoromethyl-2,3-dihydro-4-furyl group, 5-methyl-2,3-dihydro-4-furyl group, and 5-ethyl-2,3-dihydro-4-furyl group.

When R is represented by general formula (A12), the general formula (A12) represents a 4-isothiazolyl group in which R5 at the third position represents a trifluoromethyl group, a difluoromethyl group, a methyl group, an ethyl group, or a halogen atom. Examples of such a 4-isothiazolyl group include a 3-trifluoromethyl-4-isothiazolyl group, 3-difluoromethyl-4-isothiazolyl group, 3-methyl-4-isothiazolyl group, 3-ethyl-4-isothiazolyl group, 3-fluoro-4-isothiazolyl group, 3-chloro-4-isothiazolyl group, 3-bromo-4-isothiazolyl group, and 3-iodo-4-isothiazolyl group.

Each of R1, R2, R3, and R4 may be a hydrogen atom. Examples of an alkyl group represented by R1, R2, R3, or R4 include linear or branched alkyl groups of 1 to 12 carbon atoms such as methyl, ethyl, propyl, isopropyl, butyl, isobutyl, sec-butyl, tert-butyl, hexyl, decyl, and dodecyl groups.

According to the hydrogenation in the present invention, a 2-alkyl-3-aminothiophene derivative represented by general formula (2) is produced by reducing a compound represented by general formula (1):

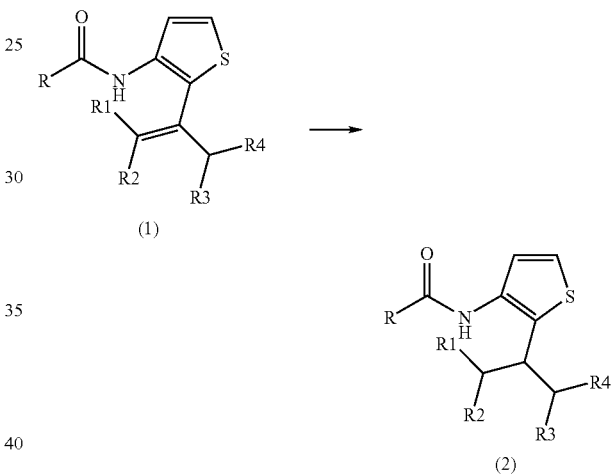

(wherein R, R1, R2, R3, and R4 are as defined above).

The compound represented by general formula (1) is composed of four isomers represented by general formulae (1a) to (1d):

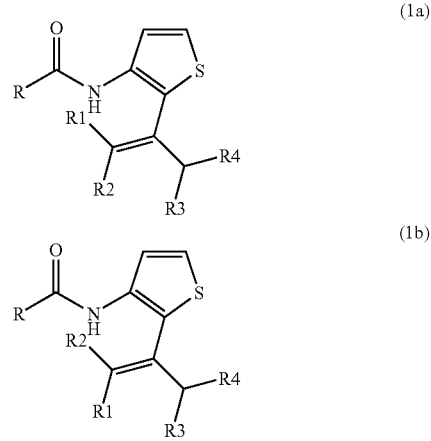

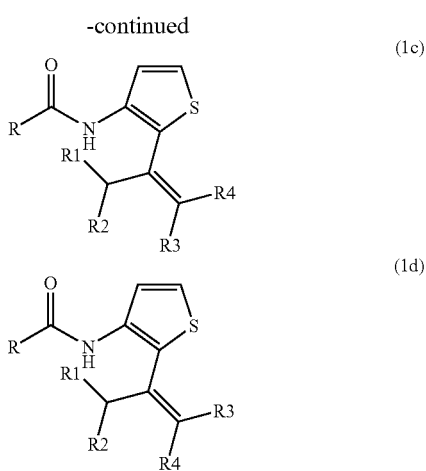

(wherein R, R1, R2, R3, and R4 are as defined above) and exists as a mixture of these 2-alkenyl-3-aminothiophene derivatives.

The reaction in the present invention can be performed by a generally known method such as a method under a slight pressure or a high-pressure hydrogenation using an autoclave (for example, described in Shin Jikken Kagaku Kouza (New Experimental Chemistry Course), Vol. 15, Oxidation and Reduction [II], Maruzen Co., Ltd, (1977)).

The catalyst used in the present invention includes a noble metal catalyst generally used for catalytic reduction. Examples of the catalyst include platinum group metals such as palladium, platinum, rhodium, ruthenium, and osmium. Although such a catalyst can be used in a metal state, the catalyst is generally used as a supported catalyst in which the metal is carried on the surface of a support such as carbon (activated carbon), barium sulfate, silica gel, alumina, and Celite. The content (carried %) of the noble metal in the catalyst used in the hydrogenation is generally 1% to 20%. Although the amount of catalyst used is not particularly limited, the content of the carried metal is generally 0.05 to 2.5 weight percent, preferably 0.025 to 0.5 weight percent of the mixture composed of the compound represented by general formula (1).

The catalyst used in the method of the present invention may be a new catalyst, a recovered catalyst used in the previous reaction, or a mixture thereof.

Examples of the solvent used according to need in the present invention include alcohols of 1 to 8 carbon atoms such as methanol, ethanol, and octanol; aliphatic hydrocarbons such as hexane and petroleum ether; aromatic hydrocarbons such as benzene, toluene, and anisole; ethers such as dioxane, tetrahydrofuran, and diethyl ether; esters such as ethyl acetate; aliphatic carboxylic acids such as acetic acid and propionic acid; and aprotic polar solvents such as dimethylformamide and dimethylsulfoxide. These solvents may be used in combination.

The amount of solvent used in the present invention is generally 0.1 to 200 mL, preferably, 2 to 20 mL relative to 1 g of the mixture composed of the compound represented by general formula (1).

The reaction temperature of the present invention is particularly important. Regarding the reaction substrate used in the present invention, when the reaction substrate has a sulfur atom and other portions that are hydrogenated, the reaction is generally performed at 100° C. or less in a known art in order to suppress the side reaction. Because of the poisoning of the sulfur, the catalyst cannot generally be recovered to reuse. Thus, there is no known art in which the catalyst is recovered for reuse. However, when the reaction is performed at 150° C. to 300° C., which is the temperature condition of the present invention, by-products due to the side reaction are not generated. Furthermore, even when the recovered catalyst is reused repeatedly, the reaction can be completed. The reaction temperature in the present invention is generally 150° C. to 300° C., preferably, 160° C. to 220° C. This temperature is applied to both a reaction performed using a new catalyst (the catalyst recovered in this reaction is reused) and a reaction preformed reusing the recovered catalyst.

The hydrogen pressure in the present invention may be normal pressure or pressurized. When the reaction is performed in a pressurized atmosphere, the pressure is 0.098 to 30 MPa, preferably, 0.098 to 3.0 MPa.

The reaction time in the present invention is generally 0.5 to 100 hours, preferably, 1 to 20 hours.

Various conditions for the catalytic hydrogenation, for example, the kind and the amount of catalyst used, the kind and the amount of solvent used, the reaction temperature, the reaction pressure, and the reaction time can be adequately selected from the numeric values in the normal range and those in the preferable range described for each condition, and can be combined with each other.

The compound represented by general formula (2) generated after hydrogenation, i.e., a 2-alkyl-3-aminothiophene derivative, can be prepared by filtering to remove the catalyst from the reaction mixture. The resultant mixture can be used for a subsequent process such as hydrolysis without further treatment. Alternatively, after the catalyst is removed, the resultant mixture may be concentrated. Subsequently, the compound can be isolated by crystallization.

The amount of noble metal catalyst reused is generally 10 to 100 weight percent, preferably, 30 to 100 weight percent, more preferably, 50 to 100 weight percent, still more preferably, 80 to 100 weight percent, and most preferably, 100 weight percent of the recovered weight.

In the present invention, the recovering of the catalyst is performed as follows: After the reaction, the catalyst is separated from the reaction solution by, for example, filtration. During filtration, the catalyst may be washed with a solvent according to need. In general, the catalyst may be recovered at about room temperature. For example, when the viscosity of the reaction mixture is too high at room temperature, the filtration and the washing may be performed at room temperature or a higher temperature according to need.

Although Examples are shown to describe the present invention more specifically, the present invention is not limited to the Examples.

The conditions for high performance liquid chromatography (HPLC) used to determine the reaction yield described in the present Examples are as follows: An aqueous solution of acetonitrile (50 volume percent) was used as the mobile phase. The flow rate of the mobile phase was controlled to 1.0 mL/min. with an LC-10 pump (available from Shimadzu Corporation). An L-Column ODS (4.6 mm in diameter×250 mm, available from Chemicals Evaluation and Research Institute, Japan) was used as the separation column. The detection was performed with a SPD-10A detector (available from Shimadzu Corporation) with a detection wavelength of 254 nm. The compounds were quantitatively determined under the above conditions.

EXAMPLE 1

N-[2-(1,3-dimethylbutenyl)thiophen-3-yl] benzoic acid amide (10 g, 35.0 mmol) and octanol (90 g) were charged in a 300-mL autoclave. Furthermore, 0.5 g dry weight (5% of the compound) of palladium-carbon (E106 NN/W available from Degussa) was charged in the autoclave and the autoclave was then sealed. Deaeration and purging were repeated five times under a nitrogen pressure of 0.2 MPa, and the pressure in the autoclave was then returned to normal pressure. The autoclave was pressurized to 0.8 MPa with hydrogen, and was then heated to 200° C. while stirring to perform hydrogenation. Two hours later, the heating was stopped. The autoclave was cooled to 30° C. or less and was then deaerated. Nitrogen purging was performed five times under a pressurized atmosphere. The autoclave was opened and the reaction mixture was filtered to separate the catalyst. Furthermore, the catalyst was washed with methanol. After the catalyst was removed, the resultant reaction mixture was analyzed by HPLC. N-[2-(1,3-dimethylbutyl)thiophen-3-yl] benzoic acid amide represented by general formula (1A5), wherein the double bond at the alkenyl portion of the starting material is hydrogenated, was produced with a yield of 97.4 molar percent (selectivity 98.9%).

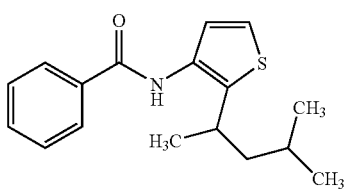

(1A5)

EXAMPLE 2

The reaction was repeated as in Example 1. However, in this reaction, a catalyst including 80% of the recovered catalyst (0.67 g, i.e., 0.4 g dry weight of the catalyst), which was prepared by filtering in Example 1, and 0.1 g dry weight of the new catalyst (1% of the compound) was used. The atmosphere in the autoclave was purged with nitrogen. Subsequently, the autoclave was pressurized to 0.8 MPa with hydrogen, and was heated to 200° C. while stirring to perform hydrogenation for 8 hours. The subsequent process was performed as in Example 1 to determine the yield. The compound represented by general formula (1A5) was produced with a yield of 95.5 molar percent (selectivity 96.3%).

EXAMPLE 3

The reaction was repeated as in Example 2. In this reaction, a catalyst including 80% of the recovered catalyst (0.56 g, i.e., 0.4 g dry weight of the catalyst), which was prepared by filtering in Example 2, and 0.1 g dry weight of the new catalyst (1% of the compound) was used. The atmosphere in the autoclave was purged with nitrogen. Subsequently, the autoclave was pressurized to 0.8 MPa with hydrogen, and was heated to 200° C. while stirring to perform hydrogenation for 8 hours. The subsequent process was performed as in Example 1 to determine the yield. The compound represented by general formula (1A5) was produced with a yield of 94.5 molar percent (selectivity 95.1%).

EXAMPLE 4

The reaction was repeated as in Example 3. However, in this reaction, all the recovered catalyst (0.60 g, i.e., 0.5 g dry weight of the catalyst), which was prepared by filtering in Example 3, was used and no new catalyst was added. The atmosphere in the autoclave was purged with nitrogen. Subsequently, the autoclave was pressurized to 0.8·MPa with hydrogen, and was heated to 200° C. while stirring to perform hydrogenation for 8 hours. The subsequent process was performed as in Example 1 to determine the yield. The compound represented by general formula (1A5) was produced with a yield of 93.6 molar percent (selectivity 94.8%).

EXAMPLE 5

The reaction was repeated as in Example 3. In this reaction, a catalyst including 80% of the recovered catalyst (0.56 g, i.e., 0.4 g dry weight of the catalyst), which was prepared by filtering in Example 4, and 0.1 g dry weight of the new catalyst (1% of the compound) was used. The atmosphere in the autoclave was purged with nitrogen. Subsequently, the autoclave was pressurized to 0.8 MPa with hydrogen, and was heated to 200° C. while stirring to perform hydrogenation for 8 hours. The subsequent process was performed as in Example 1 to determine the yield. The compound represented by general formula (1A5) was produced with a yield of 94.3. molar percent (selectivity 94.6%).

EXAMPLE 6

N-[2-(1,3-dimethylbutenyl)thiophen-3-yl]-3-trifluoromethyl-1-methylpyrazole-4-carboxylic acid amide (10 g, 28.0 mmol) and octanol (90 g) were charged in a 300-mL autoclave. Furthermore, 0.5 g dry weight (5% of the compound) of palladium-carbon (E106 NN/W available from Degussa) was charged in the autoclave and the autoclave was then sealed. Deaeration and purging were repeated five times under a nitrogen pressure of 0.2 MPa, and the pressure in the autoclave was then returned to normal pressure. The autoclave was pressurized to 0.8 MPa with hydrogen, and was then heated to 200° C. while stirring to perform hydrogenation for 2 hours. The subsequent process was performed as in Example 1 to determine the yield. N-[2-(1,3-dimethylbutyl)thiophen-3-yl]-3-trifluoromethyl-1-methylpyrazole-4-carboxylic acid amide represented by general formula (1A1) was produced with a yield of 98.1 molar percent (selectivity 98.6%).

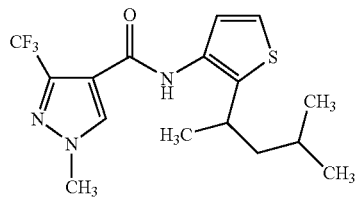

(1A1)

EXAMPLE 7

The reaction was repeated as in Example 6. However, in this reaction, a catalyst including 80% of the recovered catalyst (0.63 g, i.e., 0.4 g dry weight of the catalyst), which was prepared by filtering in Example 6, and 0.1 g dry weight of the new catalyst (1% of the compound) was used. The atmosphere in the autoclave was purged with nitrogen. Subsequently, the autoclave was pressurized to 0.8 MPa with hydrogen, and was heated to 200° C. while stirring to perform hydrogenation for 8 hours. The subsequent process was performed as in Example 1 to determine the yield. The compound represented by general formula (1A1) was produced with a yield of 96.6 molar percent (selectivity 97.8%).

EXAMPLE 8

The reaction was repeated as in Example 7. In this reaction, a catalyst including 80% of the recovered catalyst (0.56 g, i.e., 0.4 g dry weight of the catalyst), which was prepared by filtering in Example 7, and 0.1 g dry weight of the new catalyst (1% of the compound) was used. The atmosphere in the autoclave was purged with nitrogen. Subsequently, the autoclave was pressurized to 0.8 MPa with hydrogen, and was heated to 200° C. while stirring to perform hydrogenation for 8 hours. The subsequent process was performed as in Example 1 to determine the yield. The compound represented by general formula (1A1) was produced with a yield of 95.2 molar percent (selectivity 96.0%).

EXAMPLE 9

The reaction was performed as in Example 1. In this reaction, 0.5 g dry weight (5% of the compound) of palladium-carbon (E106 NN/W available from Degussa) was used as the catalyst, and octanol was used as the solvent. The reaction was performed at 180° C. for 6 hours. The subsequent process was performed as in Example 1 to determine the yield. The compound represented by general formula (1A5) was produced with a yield of 97.3 molar percent (selectivity 99.1%). Subsequently, the reaction was performed at 180° C. for 10 hours using all the catalyst recovered from the above reaction system, and the yield was determined. The compound represented by general formula (1A5) was produced with a yield of 88.7 molar percent (selectivity 98.8%). Furthermore, the reaction in the second catalyst recycle was performed at 180° C. for 8 hours using all the catalyst recovered from the above reaction system, and the yield was determined. The compound represented by general formula (1A5) was produced with a yield of 84.8 molar percent (selectivity 99.0%). Although the reaction using the recovered catalyst was stopped after 8 hours, the reaction itself still proceeded. Therefore, if the reaction time had been extended, the yield could have been increased.

EXAMPLE 10

N-[2-(1,3-dimethylbutenyl)thiophen-3-yl] benzoic acid amide (10 g, 35.0 mmol) and 2-propanol (90 g) were charged in a 300-mL autoclave. Furthermore, 0.5 g dry weight (5% of the compound) of palladium-carbon (E106 NN/W available from Degussa) was charged in the autoclave and the autoclave was then sealed. Deaeration and purging were repeated five times under a nitrogen pressure of 0.2 MPa, and the pressure in the autoclave was then returned to normal pressure. The autoclave was pressurized to 3 MPa with hydrogen, and was then heated to 200° C. while stirring to perform hydrogenation. Six hours later, the heating was stopped. The autoclave was cooled to 30° C. or less and was then deaerated. Nitrogen purging was performed five times at under a pressurized atmosphere. The autoclave was opened and the reaction mixture was filtered to separate the catalyst. Furthermore, the catalyst was washed with methanol. After the catalyst was removed, the resultant reaction mixture was analyzed by HPLC. N-[2-(1,3-dimethylbutyl)thiophen-3-yl] benzoic acid amide represented by general formula (1A5), wherein the double bond at the alkenyl portion of the starting material is hydrogenated, was produced with a yield of 94.3 molar percent (selectivity 95.0%).

EXAMPLE 11

The reaction was repeated as in Example 10. However, in this reaction, a catalyst including 80% of the recovered catalyst (0.67 g, i.e., 0.4 g dry weight of the catalyst), which was prepared by filtering in Example 10, and 0.1 g dry weight of the new catalyst (1% of the compound) was used. The atmosphere in the autoclave was purged with nitrogen. Subsequently, the autoclave was pressurized to 3 MPa with hydrogen, and was heated to 200° C. while stirring to perform hydrogenation for 6 hours. The subsequent process was performed as in Example 1 to determine the yield. The compound represented by general formula (1A5) was produced with a yield of 92.5 molar percent (selectivity 94.1%).

EXAMPLE 12

The reaction was repeated as in Example 10. In this reaction, a catalyst including 80% of the recovered catalyst (0.66 g, i.e., 0.4 g dry weight of the catalyst), which was prepared by filtering in Example 11, and 0.1 g dry weight of the new catalyst (1% of the compound) was used. The atmosphere in the autoclave was purged with nitrogen. Subsequently, the autoclave was pressurized to 3 MPa with hydrogen, and was heated to 200° C. while stirring to perform hydrogenation for 6 hours. The subsequent process was performed as in Example 1 to determine the yield. The compound represented by general formula (1A5) was produced with a yield of 91.8 molar percent (selectivity 94.1%).

EXAMPLE 13

N-[2-(1,3-dimethylbutenyl)thiophen-3-yl] benzoic acid amide (10 g, 35.0 mmol) and 1-butanol (90 g) were charged in a 300-mL autoclave. Furthermore, 0.5 g dry weight (5% of the compound) of palladium-carbon (E106 NN/W available from Degussa) was charged in the autoclave and the autoclave was then sealed. Deaeration and purging were repeated five times under a nitrogen pressure of 0.2 MPa, and the pressure in the autoclave was then returned to normal pressure. The autoclave was pressurized to 3 MPa with hydrogen, and was then heated to 200° C. while stirring to perform hydrogenation. Four hours later, the heating was stopped. The autoclave was cooled to 30° C. or less and was then deaerated. Nitrogen purging was performed five times under a pressurized atmosphere. The autoclave was opened and the reaction mixture was filtered to separate the catalyst. Furthermore, the catalyst was washed with methanol. After the catalyst was removed, the resultant reaction mixture was analyzed by HPLC. N-[2-(1,3-dimethylbutyl)thiophen-3-yl] benzoic acid amide represented by general formula (1A5), wherein the double bond at the alkenyl portion of the starting material is hydrogenated, was produced with a yield of 93.1 molar percent (selectivity 97.9%).

EXAMPLE 14

The reaction was repeated as in Example 13. However, in this reaction, a catalyst including 80% of the recovered catalyst (0.65 g, i.e., 0.4 g dry weight of the catalyst), which was prepared by filtering in Example 10, and 0.1 g dry weight of the new catalyst (1% of the compound) was used. The atmosphere in the autoclave was purged with nitrogen. Subsequently, the autoclave was pressurized to 3 MPa with hydrogen, and was heated to 200° C. while stirring to perform hydrogenation for 6 hours. The subsequent process was performed as in Example 1 to determine the yield. The compound represented by general formula (1A5) was produced with a yield of 94.0 molar percent (selectivity 98.9%).

EXAMPLE 15

The reaction was repeated as in Example 13. In this reaction, a catalyst including 80% of the recovered catalyst (0.58 g, i.e., 0.4 g dry weight of the catalyst), which was prepared by filtering in Example 11, and 0.1 g dry weight of the new catalyst (1% of the compound) was used. The atmosphere in the autoclave was purged with nitrogen. Subsequently, the autoclave was pressurized to 3 MPa with hydrogen, and was heated to 200° C. while stirring to perform hydrogenation for 6 hours. The subsequent process was performed as in Example 1 to determine the yield. The compound represented by general formula (1A5) was produced with a yield of 93.4 molar percent (selectivity 98.4%).

Comparative Example 1

The reaction was performed as in Example 1. In this reaction, 0.5 g dry weight (5% of the compound) of palladium-carbon (E106 NN/W available from Degussa) was used as the catalyst. However, methanol was used as the solvent, and the reaction was performed at 30° C. for 7 hours. The subsequent process was performed as in Example 1 to determine the yield. The compound represented by general formula (1A5) was produced with a yield of 98.7 molar percent (selectivity 99.2%). Subsequently, all the catalyst recovered from the above reaction system, and in addition, 0.1 g dry weight of the new catalyst (1% of the compound) were charged. The reaction was then performed at 30° C. for 9 hours. However, hydrogen was barely absorbed from 7 hours onward and the reaction was completed. The subsequent process was performed as in Example 1 to determine the yield. The yield of the compound represented by general formula (1A5) was not more than 84.3 molar percent (selectivity 98.8%).

Comparative Example 2

The reaction was performed as in Example 1. In this reaction, 0.5 g dry weight (5% of the compound) of palladium-carbon (E106 NN/W available from Degussa) was used as the catalyst. However, methanol was used as the solvent, and the reaction was performed at 100° C. for 1 hour. The subsequent process was performed as in Example 1 to determine the yield. The compound represented by general formula (1A5) was produced with a yield of 88.1 molar percent (selectivity 98.9%). Subsequently, the reaction was performed at 100° C. in the same way using all the catalyst recovered from the above reaction system. After the reaction had been performed for 1 hour, it had already reached a steady state. The subsequent process was performed as in Example 1 to determine the yield. The yield of the compound represented by general formula (1A5) was not more than 12.7 molar percent (selectivity 99.9%).

Comparative Example 3

The reaction was performed as in Example 1. However, in this reaction, 1.0 g dry weight (10% of the compound) of palladium-carbon (S-Type available from N.E. Chemcat Corporation) was used as the catalyst, and methanol was used as the solvent. The reaction was performed at 100° C. for 1 hour. The subsequent process was performed as in Example 1 to determine the yield. The compound represented by general formula (1A5) was produced with a yield of 99.1 molar percent (selectivity 99.3%). Subsequently, the reaction was performed in the same way at 100° C. for 1 hour using all the catalyst recovered from the above reaction system, and the yield was determined. The compound represented by general formula (1A5) was produced with a yield of 91.9 molar percent (selectivity 98.1%). Furthermore, the reaction in the second catalyst recycle was performed at 100° C. for 1 hour using all the catalyst recovered from the above reaction system, and the yield was determined. The compound represented by general formula (1A5) was produced with a yield of 46.8 molar percent (selectivity 97.7%). Furthermore, the reaction in the third catalyst recycle was performed at 100° C. for 1 hour using all the catalyst recovered from the above reaction system. After the reaction had been performed for 1 hour, the absorption of hydrogen had already stopped. The reaction was stopped, and the subsequent process was then performed to determine the yield. The yield of the compound represented by general formula (1A5) was not more than 32.1 molar percent (selectivity 98.8%).

Comparative Example 4

The reaction was performed as in Example 1. However, in this reaction, 1.0 g dry weight (10% of the compound) of Raney-Ni (R-239 available from Nikko Rica Corporation) was used as the catalyst, and a xylene was used as the solvent. The autoclave was sealed and nitrogen-purging was repeated five times. The pressure in the autoclave was then returned to normal pressure. The autoclave was pressurized to 2.0 MPa with hydrogen, and was then heated to 160° C. while stirring to perform hydrogenation for 12 hours. After the catalyst was removed, the resultant reaction mixture was analyzed by HPLC. The yield of the compound represented by general formula (1A5) was not more than 61.0 molar percent (selectivity 79.0%).

Comparative Example 5

The reaction was performed as in Example 1. However, in this reaction, 2.0 g dry weight (20% of the compound) of a copper catalyst (VF300-1 available from Nikko Rica Corporation) was used, and octanol was used as the solvent. The autoclave was sealed and nitrogen purging was repeated five times. The pressure in the autoclave was then returned to normal pressure. The autoclave was pressurized to 2.0 MPa with hydrogen, and was then heated to 200° C. while stirring to perform hydrogenation for 18 hours. After the catalyst was removed, the resultant reaction mixture was analyzed by HPLC. The yield of the compound represented by general formula (1A5) was not more than 76.3 molar percent (selectivity 84.9%).

Reference Example 1

It was assumed that the catalyst was inactivated because the compound before hydrogenation or the reaction product was adhered to the catalyst. Therefore, the sulfur (S) content in the catalyst was measured. The sulfur content in the catalyst recovered in Example 1, which was used once in the reaction performed at 200° C., was 1.2%. The sulfur content in the catalyst recovered in Example 3, which was used three times, was 1.6%.

Reference Example 2

In Comparative Example 3, the sulfur content in the catalyst used once in the reaction performed at 100° C. and then recovered was 1.6%. In addition, the sulfur content in the catalyst used three times and then recovered was 3.1%. This result showed that the sulfur content after the reaction performed at 100° C. was significantly increased, compared with that after the reaction performed at 200° C. (Reference Example 1).

INDUSTRIAL APPLICABILITY

According to the present invention, in the industrial scale production of a compound such as a 2-alkyl-3-aminothiophene derivative represented by general formula (2) by reducing a sulfur-containing compound, for example, represented by general formula (1), by hydrogenation in the presence of a noble metal catalyst, the noble metal catalyst can be recycled to economical advantage. Consequently, the present invention also provides higher economical efficiency in the production of the compound represented by general formula (2).

According to the production method of the present invention, the reduction by hydrogenation performed at a relatively high temperature suppresses the inactivation of the noble metal catalyst. Consequently, the method of the present invention allows the noble metal catalyst to be recovered for reuse. The present invention provides an industrial scale method for producing the compound, for example, represented by general formula (2), with economical efficiency.

The invention claimed is:

1. A method for reducing a sulfur-containing compound by hydrogenation, the method comprising the steps of:
   hydrogenating the sulfur-containing compound using a noble metal catalyst at a reaction temperature of 150° C. to 300° C.;
   recovering the used noble metal catalyst; and
   reusing the noble metal catalyst.

2. The method according to claim 1, wherein the noble metal catalyst comprises palladium.

3. The method according to claim 1, wherein an alcohol of 1 to 8 carbon atoms is used as a reaction solvent in the step of hydrogenating the sulfur-containing compound.

4. The method according to claim 3, wherein the sulfur-containing compound is a thiophene compound.

5. The method according to claim 4, wherein the thiophene compound is a thiophene amide.

6. The method according to claim 5, wherein the thiophene amide is represented by general formula (1):

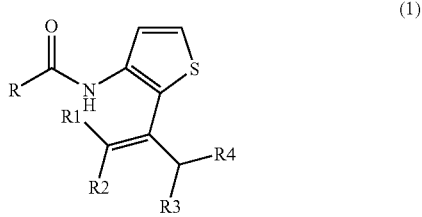

(wherein R represents a hydrogen atom, a substituted or unsubstituted alkyl group, a substituted or unsubstituted alkoxy group, a substituted or unsubstituted aromatic hydrocarbon ring, a substituted or unsubstituted nonaromatic hydrocarbon ring, a substituted or unsubstituted aromatic heterocycle, or a substituted or unsubstituted nonaromatic heterocycle; R1, R2, R3, and R4 independently represent a hydrogen atom, or a linear or branched alkyl group of 1 to 12 carbon atoms; and R1 and R2, R3 and R4, R1 and R3, R1 and R4, R2 and R3, or R2 and R4 may be bonded together to form a cycloalkyl group), and an alkenyl group of the compound represented by general formula (1) is reduced by hydrogenation to produce a 2-alkyl-3-aminothiophene derivative represented by general formula (2):

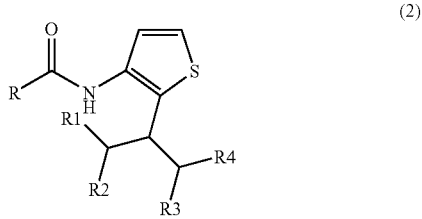

(wherein R, R1, R2, R3, and R4 are as defined above).

7. The method according to claim 6, wherein R in the compounds represented by general formula (1) and general formula (2) is a hydrogen atom, a substituted or unsubstituted alkyl group, a substituted or unsubstituted alkoxy group, or a substituted or unsubstituted phenyl group.

8. The method according to claim 6, wherein R in the compounds represented by general formula (1) and general formula (2) is a group represented by general formulae (A1) to (A12):

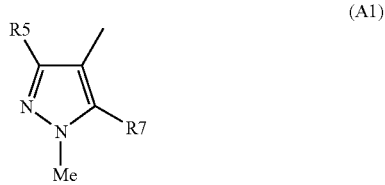

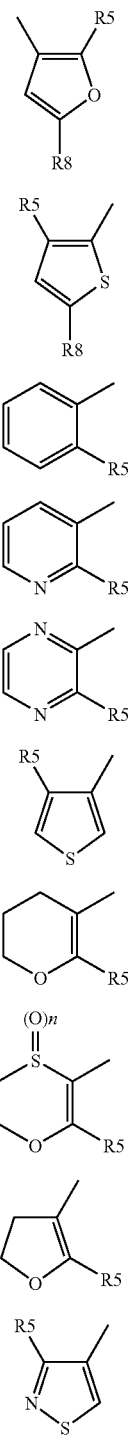

(A3)
(A4)
(A5)
(A6)
(A7)
(A8)
(A9)
(A10)
(A11)
(A12)

(wherein R5 represents a trifluoromethyl group, a difluoromethyl group, a methyl group, an ethyl group, a hydrogen atom, or a halogen atom; R6 represents a hydrogen atom, a methyl group, a trifluoromethyl group, a halogen atom, a methoxy group, or an amino group; R7 represents a hydrogen atom, a halogen atom, a methyl group, or a methoxy group; R8 represents a hydrogen atom, a methyl group, an ethyl group, or a halogen atom; and n represents an integer of 0 to 2; however, in general formulae (A9), (A10), and (A11), R5 does not represent a halogen atom).

9. The method according to claim 8, wherein R in the compounds represented by general formula (1) and general formula (2) is represented by general formula (A1) in which R5 is a trifluoromethyl group and R7 is a hydrogen atom.

10. The method according to claim 6, wherein each of R1, R2, and R3 in the compound represented by general formula (2) is a hydrogen atom and R4 in the compound represented by general formula (2) is an isopropyl group.

11. The method according to claim 2, wherein the sulfur-containing compound is a thiophene compound.

12. The method according to claim 11, wherein the thiophene compound is a thiophene amide.

13. The method according to claim 12, wherein the thiophene amide is represented by general formula (1):

(1)

(wherein R represents a hydrogen atom, a substituted or unsubstituted alkyl group, a substituted or unsubstituted alkoxy group, a substituted or unsubstituted aromatic hydrocarbon ring, a substituted or unsubstituted nonaromatic hydrocarbon ring, a substituted or unsubstituted aromatic heterocycle, or a substituted or unsubstituted nonaromatic heterocycle; R1, R2, R3, and R4 independently represent a hydrogen atom, or a linear or branched alkyl group of 1 to 12 carbon atoms; and R1 and R2, R3 and R4, R1 and R3, R1 and R4, R2 and R3, or R2 and R4 may be bonded together to form a cycloalkyl group), and an alkenyl group of the compound represented by general formula (1) is reduced by hydrogenation to produce a 2-alkyl-3-aminothiophene derivative represented by general formula (2):

(2)

(wherein R, R1, R2, R3, and R4 are as defined above).

14. The method according to claim 13, wherein R in the compounds represented by general formula (1) and general formula (2) is a hydrogen atom, a substituted or unsubstituted alkyl group, a substituted or unsubstituted alkoxy group, or a substituted or unsubstituted phenyl group.

15. The method according to claim 13, wherein R in the compounds represented by general formula (1) and general formula (2) is a group represented by general formulae (A1) to (A12):

(A1) 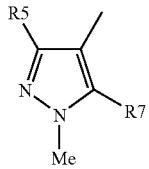

(A2) 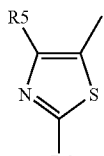

(A3) 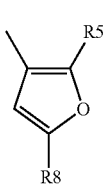

(A4) 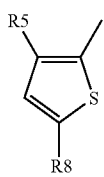

(A5) 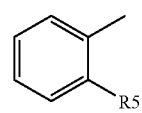

(A6) 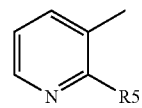

(A7) 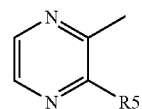

(A8) 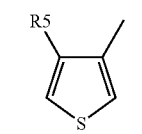

(A9) 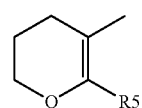

(A10) 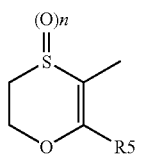

(A11) 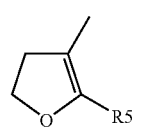

-continued (A12) 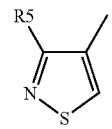

(wherein R5 represents a trifluoromethyl group, a difluoromethyl group, a methyl group, an ethyl group, a hydrogen atom, or a halogen atom; R6 represents a hydrogen atom, a methyl group, a trifluoromethyl group, a halogen atom, a methoxy group, or an amino group; R7 represents a hydrogen atom, a halogen atom, a methyl group, or a methoxy group; R8 represents a hydrogen atom, a methyl group, an ethyl group, or a halogen atom; and n represents an integer of 0 to 2; however, in general formulae (A9), (A10), and (A11), R5 does not represent a halogen atom).

16. The method according to claim 15, wherein R in the compounds represented by general formula (1) and general formula (2) is represented by general formula (A1) in which R5 is a trifluoromethyl group and R7 is a hydrogen atom.

17. The method according to claim 13, wherein each of R1, R2, and R3 in the compound represented by general formula (2) is a hydrogen atom and R4 in the compound represented by general formula (2) is an isopropyl group.

18. The method according to claim 1, wherein the sulfur-containing compound is a thiophene compound.

19. The method according to claim 18, wherein the thiophene compound is a thiophene amide.

20. The method according to claim 19, wherein the thiophene amide is represented by general formula (1):

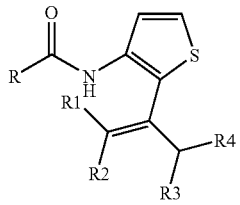

(1)

(wherein R represents a hydrogen atom, a substituted or unsubstituted alkyl group, a substituted or unsubstituted alkoxy group, a substituted or unsubstituted aromatic hydrocarbon ring, a substituted or unsubstituted nonaromatic hydrocarbon ring, a substituted or unsubstituted aromatic heterocycle, or a substituted or unsubstituted nonaromatic heterocycle; R1, R2, R3, and R4 independently represent a hydrogen atom, or a linear or branched alkyl group of 1 to 12 carbon atoms; and R1 and R2, R3 and R4, R1 and R3, R1 and R4, R2 and R3, or R2 and R4 may be bonded together to form a cycloalkyl group), and an alkenyl group of the compound represented by general formula (1) is reduced by hydrogenation to produce a 2-alkyl-3-aminothiophene derivative represented by general formula (2):

(2)

(wherein R, R1, R2, R3, and R4 are as defined above).

21. The method according to claim 20, wherein R in the compounds represented by general formula (1) and general formula (2) is a hydrogen atom, a substituted or unsubstituted alkyl group, a substituted or unsubstituted alkoxy group, or a substituted or unsubstituted phenyl group.

22. The method according to claim 20, wherein R in the compounds represented by general formula (1) and general formula (2) is a group represented by general formulae (A1) to (A12):

(A1)

(A2)

(A3)

(A4)

(A5)

(A6)

(A7)

(A8)

(A9)

(A10)

(A11)

(A12)

(wherein R5 represents a trifluoromethyl group, a difluoromethyl group, a methyl group, an ethyl group, a hydrogen atom, or a halogen atom; R6 represents a hydrogen atom, a methyl group, a trifluoromethyl group, a halogen atom, a methoxy group, or an amino group; R7 represents a hydrogen atom, a halogen atom, a methyl group, or a methoxy group; R8 represents a hydrogen atom, a methyl group, an ethyl group, or a halogen atom; and n represents an integer of 0 to 2; however, in general formulae (A9), (A10), and (A11), R5 does not represent a halogen atom).

23. The method according to claim 22, wherein R in the compounds represented by general formula (1) and general formula (2) is represented by general formula (A1) in which R5 is a trifluoromethyl group and R7 is a hydrogen atom.

24. The method according to claim 20, wherein each of R1, R2, and R3 in the compound represented by general formula (2) is a hydrogen atom and R4 in the compound represented by general formula (2) is an isopropyl group.

* * * * *